United States Patent [19]

Asahi et al.

[11] Patent Number: 4,839,285

[45] Date of Patent: Jun. 13, 1989

[54] METHOD FOR PRODUCTION OF CYTIDINE AND/OR DEOXYCYTIDINE

[75] Inventors: Satoru Asahi; Yutaka Tsunemi, both of Suita; Muneharu Doi, Takarazuka, all of Japan

[73] Assignee: Takeda Chemical Industries, Ltd., Osaka, Japan

[21] Appl. No.: 802,344

[22] Filed: Nov. 25, 1985

[30] Foreign Application Priority Data

Dec. 6, 1984 [JP] Japan .................................. 59-258788

[51] Int. Cl.[4] .................... C12P 19/38; C12R 1/07; C12N 15/00
[52] U.S. Cl. .................... 435/87; 435/252.5; 435/172.1; 435/839
[58] Field of Search .............. 435/89, 839, 122, 172.1, 435/87, 253

[56] References Cited

FOREIGN PATENT DOCUMENTS 21499 11/1961 Japan .................................. 435/87
3621499 11/1961 Japan .................................. 435/87
5130989 11/1977 Japan .................................. 435/87

OTHER PUBLICATIONS

Neuhard, J., Abstract of ASM Annual Meeting, 1977, No. H-94.
Kato et al., Appl. and Environ. Microbiol., vol. 34, 1977, pp. 689–694.
Central Patents Index, Derwent 1978, 89080Y/50.
Central Patents Index, Derwent 1978, 89081Y/80.

*Primary Examiner*—Charles F. Warren
*Assistant Examiner*—Irene Marx
*Attorney, Agent, or Firm*—Wenderoth, Lind & Ponack

[57] ABSTRACT

Cytidine and/or deoxycytidine are produced at high yields by culturing cytidine deaminase activity-defective microbes of the genus Bacillus, which have resistance to pyrimidine analogs and with the ability to produce cytidine and/or deoxycytidine in a medium.

10 Claims, No Drawings

METHOD FOR PRODUCTION OF CYTIDINE AND/OR DEOXYCYTIDINE

The present invention relates to a method for the production of cytidine and/or deoxycytidine, and to a new microorganism.

Cytidine and deoxycytidine are useful as raw materials for synthetic medicines. The present invention relates to (a) a method for the production of cytidine and/or deoxycytidine using fermentation, and (b) microbes of the genus Bacillus used in said method.

Well-known methods for the production of cytidine using fermentation include (a) a method using a variant of *Bacillus subtilis* or *Proteus rettgeri* (Japanese Patent Publication No. 21499/1961), (b) a method using a purine analogue-resistant line, a pyrimidine analogue-resistant line, and/or a histidine analogue-resistant line, induced from bacteria of the genus Brevibacterium (Japanese Patent Publication No. 18871/1982), and (c) a method using a purine analogue-resistant line induced from bacteria of the genus Microbacterium (Japanese Patent Publication No. 18872/1982).

However, no method is known of producing and accumulating a considerable quantity of deoxycytidine in a medium.

The present invention provides a more efficient industrial method with regard to yield, etc. for the production of cytidine and deoxycytidine.

The inventors, after many studies on bacteria producing cytidine and deoxycytidine, found that cytidine deaminase activity-defective microbes of the genus Bacillus, having pyrimidine analogue resistance, produce and accumulate a considerable quantity of cytidine and/or deoxycytidine in a medium; work was continued on the basis of this finding to complete the present invention.

The present invention consists of (1) a method for the production of cytidine and/or deoxycytidine, characterized in that cytidine deaminase activity-defective microbes of the genus Bacillus, having resistance to pyrimidine analogues and with the ability to produce cytidine and/or deoxycytidine, are cultured in a medium to collect cytidine and/or deoxycytidine produced and accumulated in the culture, and (2) cytidine deaminase activity-defective *Bacillus subtilis* having resistance to pyrimidine analogues.

In this invention, "cytidine deaminase activity-defective line," "pyrimidine analogue-resistant line," and "pyrimidine analogue," are defined respectively as follows: Cytidine deaminase activity-defective line Microbes whose cytidine deaminase activity value is less than 0.01 unit/mg-protein (enzyme power by which 1 n mole cytidine is deaminated in one minute is defined as 1 unit.), when measured in accordance with the method of D. F. Wentworth et al. ("Methods in Enzymology," Vol. LI, ed. by P. A. Hoffee and M. E. Jones, Academic Press, N.Y., 1978, p. 401), using a centrifugal supernatant fraction obtained from cells disrupted by ultrasonication. Pyrimidine analogue-resistant line Microbes induced from bacteria of the genus Bacillus, whose genetic characteristics are so changed that they can grow even in a medium containing pyrimidine analogues at too high concentration for their parent line to grow.

Pyrimidine analogue

A substance having a structure similar to that of pyrimidine bases such as uracil and cytosine; for example, 6-azauracil, 2-thiouracil, 5-fluorouracil, 5-fluoroorotic acid, and their ribosides and ribotides. A microbe having resistance to at least one of these substances is defined as a "pyrimidine analogue-resistant line."

Microbes used in this invention are *Bacillus subtilis* AU-50 (IFO 14395, FERM BP-907), *Bacillus subtilis* FU-11 (IFO 14393, FERM BP-908), *Bacillus subtilis* 6AU-500 (IFO 14407, FERM BP-909), and *Bacillus subtilis* 2TU-200 (IFO 14408, FERM BP-910).

Among these, *Bacillus subtilis* AU-50 and FU-11 lines were induced from *Bacillus subtilis* (IFO 13719, ATCC 6051), 6AU-500 and 2TU-200 lines were induced from Bacillus subtilis No. 122 (IFO 14386, FERM BP-859).

The *Bacillus subtilis* AU-50, FU-11, No. 122 strains and the *Bacillus subtilis* 6AU-500, 2TU-200 strains have been deposited on Oct. 19, 1984 and Dec. 3, 1984, respectively, at Fermentation Research Institute, Agency of Industrial Science and Technology, Ministry of International Trade and Industry (FRI), Japan under the accession number of Ferm P-7911, P-7912, P-7908, P-7971 and P-7972, the deposits being converted to deposits under the Budapest Treaty and, have been stored at FRI under the accession numbers of Ferm BP-907, BP-908, BP-909 and BP-910.

Among said parent lines, *Bacillus subtilis* (IFO 13719, ATCC 6051) is a well-known line described in List of Cultures, 1978, Sixth Edition, issued by the Institute for Fermentation, OSAKA, and in Catalogue of Strains I, Fifteenth Edition, 1982, issued by the American Type Culture Collection (ATCC), whereas *Bacillus subtilis* No. 122 (IFO 14386, FERM BP-859) is a line newly isolated from soil by the inventors. The bacteriological characteristics of No. 122 line are as follows:

A. Morphology
(1) Shape and size: Short bacillus, (0.7−0.8×2.5−3.0 μ)
(2) Polymorphism: Monotype, rarely double type
(3) Motility: No
(4) Sporulation: Yes
(5) Spore shape: Ellipsoid
(6) Spore location: Near center
(7) Gram-stain: Positive
(8) Acid resistance: No B. Growth state
(1) Meat infusion agar plate culture: Irregular and diffusive shape, surface rough flat, opaque and light brown
(2) Meat infusion broth culture: Pellicle is formed on surface. No turbidity is observed.
(3) Litmus milk: Peptonization and pigment reduction are observed.

C. Physiological characteristics
(1) Nitrate reduction: Yes
(2) V-P test: Positive
(3) Starch hydrolysis: Yes
(4) Citric acid utilization: Yes
(5) Propionic acid utilization: No
(6) Ammonium salt utilization: Yes
(7) Urease: Feeble
(8) Catalase: Present
(9) Behavior to oxygen: Aerobic
(10) Sodium chloride resistance: Growable at 7% concentration
(11) Acid resistance: Growable at pH 5.7

The said bacteriological characteristics were examined in accordance with "Bergy's Manual of Determinative Bacteriology," Eighth edition, 1974, edited by R. E. Buchanan and N. E. Gibbons; this line was then identified as being a microbe belonging to *Bacillus subtilis*.

The bacteriological characteristics of the bacteria of the genus Bacillus used in the method in this invention, which characteristics are given above, are the same as those of their parent line, except for the following: they have no cytidine deaminase activity, they have resistance to pyrimidine analogues, and they are able to produce cytidine and/or deoxycytidine.

In the present invention, using various bacteria species of the genus Bacillus other than the said microbe line as a parent line, cytidine deaminase activity-defective microbes having resistance to pyrimidine analogues and able to produce cytidine and/or deoxycytidine can be easily induced by variation-causing treatments such as ultraviolet irradiation and N-methyl-N'-nitro-N-nitrosoguanidine (NTG) treatment.

To culture bacteria producing cytidine and/or deoxycytidine as obtained in the present process, a method similar to the ordinary microbial culture method is used. That is, the medium contains carbon source, nitrogen source, metal ions, and, if necessary, sources of nutrients such as amino acids, nucleic acids, and vitamins.

As a carbon source, glucose, sucrose, maltose, starch, hydrolyzed starch liquid, molasses etc. are used. As a nitrogen source, both organic sources such as peptone, corn steep liquor, soybean powder, yeast extract, and urea, and inorganic sources such as ammonium salts of sulfuric, nitric, chloric, or carbonic acid, ammonia gas, and ammonia water are used singly or in combination, respectively. As for other nutrient sources, various minerals, amino acids, and vitamins essential to the growth of bacteria are properly used singly or in combination. In addition, deforming agents such as silicon oil and polyalkylene glycol ether, or surface-active agents can be added to a medium, if required. Bacteria are cultured usually under aerobic conditions, using shaking culture, deep aeration spinner culture or other methods. It is usually advantageous for the pH value of the medium to be within a range between 4 and 9. If change in pH value is observed during the culture process, sulfuric acid, calcium carbonate, sodium hydroxide, ammonia gas, or ammonia water can be added as necessary to correct the range. As for culture temperature, a temperature is chosen which is suitable for both the growth of microbes to be used, and for the accumulation of cytidine and/or deoxycytidine, within a range of 20° C. to 45° C. Culture is continued until the accumulated quantity of cytidine and/or deoxycytidine substantially reaches the maximum level: this is usually reached in 2~6 days.

In order to separate and collect cytidine and/or deoxycytidine from the culture, well-known refining methods are usually used, e.g., the precipitation method and chromatographic methods using ion exchange resin or activated charcoal (Agricultural and Biological Chemistry, 29, 742, 1965, etc.).

The present invention makes possible the industrially favorable production of cytidine and deoxycytidine, both of which are useful for materials of synthetic medicines. That is, the production method of this invention is characterized in that cytidine deaminase activity-defective microbes are used which are of the genus Bacillus, having resistance to pyrimidine analogues and capable of producing cytidine and/or deoxycytidine; thus, both desired substances can be obtained at higher yields than in the method using the conventional Bacillus bacteria.

Hereinafter the present invention is described more concretely, with several examples of preferred embodiments of the invention.

EXAMPLE 1

*Bacillus Subtilis* (IFO 13719, ATCC 6051), after treatment with 50 μg/ml NTG at 37° C. for 20 minutes (hereinafter NTG treatment conditions are the same), was applied to a medium prepared by adding 100 μg/ml uracil to basic medium (A), and cultured at 37° C. for 3 days. Among the colonies which appeared, an auxotroph for uracil was selected via the replica method. This uracil-requiring line, after treatment with NTG under the same conditions as above, was then applied to a medium prepared by adding 100 μg/ml uracil to basic medium (A), and cultured at 37° C. for 3 days.

| Basic Medium (A) | |
|---|---|
| Glucose | 2.0% |
| Ammonium sulfate | 0.2% |
| Potassium dihydrogenphosphate | 0.6% |
| Sodium citrate | 0.1% |
| Dipotassium hydrogenphosphate | 1.4% |
| Magnesium sulfate | 0.02% |
| Biotin | 0.1 mg/l |
| Agar (ph 7.0) | 2.0% |

The colonies which appeared were replicated to a medium obtained by adding 100 μg/ml cytidine to basic medium (A); a line which could not grow on the medium (cytidine deaminase activity-defective line) was selected. After treatment with NTG in the same manner as above, this line was applied to basic medium (A) and cultured at 37° C. for 3 days. A line was then selected from the colony produced. After treatment with NTG under the same conditions as above, this line was applied to medium (A-FU), obtained by adding 0.5 μg/ml 5-fluorouracil to basic medium (A), and cultured at 37° C. for 4 days. From the colonies produced, Bacillus subtilis FU-11 (IFO 14393, FERM BR-908) was selected as a line capable of cytidine and 2'-deoxycytidine production.

The cytidine deaminase activity (measured by the method of D. F. Wentworth et al., described above) and the pyrimidine analogue resistance of this line and ATTC 6051 are shown in Tables 1 and 2.

TABLE 1

| Line | Cytidine Deaminase Activity* |
|---|---|
| *Bacillus subtilis* FU-11 | not more than 0.01 |
| *Bacillus subtilis* ATCC 6051 | 74.7 |

*Unit/mg-protein

TABLE 2

| Additive to Basic Medium (A) and Quantity (μg/ml) | | Growability of Each Line* | |
|---|---|---|---|
| | | ATCC 6051 | FU-11 |
| None | | + | + |
| 6-azauracil | 100 | − | + |
| 2-thiouracil | 100 | − | + |
| 5-fluorouracil | 0.5 | − | + |
| 5-fluoroorotic acid | 0.5 | − | + |

*+: Growth observed
−: No growth observed

Next, these lines were inoculated into 20 ml fermentation medium consisting of 15% glucose, 3% corn steep liquor, 1% urea, and 2% calcium carbonate, contained in a 200 ml flask, and subjected to shaking culture at 37° C. for 3 days. The results are shown in Table 3.

TABLE 3

| Line | Accumulated Cytidine Quantity | Accumulated Deoxycytidine Quantity |
|---|---|---|
| Bacillus subtilis FU-11 | 5.1 mg/ml | 0.7 mg/ml |
| Bacillus subtilis ATCC 6051 | 0 mg/ml | 0 mg/ml |

EXAMPLE 2

A cytidine deaminase activity-defective line which was obtained from Bacillus subtilis (IFO 13719, ATCC 6051) in the same manner as shown in Example 1, after treatment with NTG, was applied to a medium prepared by adding 100 μg/ml 6-azauracil (concentration too high for parent line to grow on the medium) to basic medium (A); Bacillus subtilis AU-50 (IFO 14395, FERM BP-907) was selected as a line growable on such a medium. The resistance of this line to pyrimidine analogues is shown in Table 4.

TABLE 4

| Additive to Basic Medium (A) and Quantity (μg/ml) | | Growability of AU-50* |
|---|---|---|
| None | | + |
| 6-azauracil | 100 | + |
| 2-thiouracil | 100 | + |
| 5-fluorouracil | 0.5 | + |
| 5-fluoroorotic acid | 50 | + |

*+: Growth observed
−: No growth observed

An AU-50 line was cultured under the same conditions as in Example 1, 1.5 mg/ml cytidine and 2.3 mg/ml deoxycytidine being accumulated.

EXAMPLE 3

As in Example 1, an auxotroph for uracil was obtained from Bacillus subtilis No. 122 (IFO 14386, FERM BP-859), and then a line both cytidine deaminase activity-defective and whose auxotrophic requirement for uracil reversed. This variant, after treatment with NTG, was applied to a medium prepared by adding 200 μg/ml 2-thiouracil (concentration too high for parent line to grow on the medium) to basic medium (A) as shown in Example 1; Bacillus subtilis 2TU-200 (IFO 14408, FERM BP-910) was selected as a line growable on such a medium. Its cytidine deaminase activity value was 0.01 unit/mg-protein. (NB: That of the parent line as 55.8 unit/mg-protein.) The resistance of these lines to pyrimidine analogues is shown in Table 5.

TABLE 5

| Additive to Basic Medium (A) and Quantity (μg/ml) | | Growability of Each Line* | |
|---|---|---|---|
| | | No. 122 | 2TU-200 |
| None | | + | + |
| 6-azauracil | 200 | − | + |
| 2-thiouracil | 200 | − | + |
| 5-fluorouracil | 0.5 | − | + |
| 5-fluoroorotic acid | 50 | − | + |

*+: Growth observed
−: No growth observed

Next, Bacillus subtilis 2TU-200 was cultured under the same conditions as in Example 1; 1.5 mg/ml cytidine and 0.6 mg/ml deoxycytidine were accumulated.

EXAMPLE 4

A cytidine deaminase-defective line which lost its uracil auxotrophism, which had been obtained from Bacillus subtilis No. 122 (IFO 14386, FERM BP-859) as in Example 3, after treatment with NTG as in Example 1, was applied to a medium prepared by adding 200 μg/ml 6-azauracil (concentration too high for parent line to grow) to basic medium (A) as shown in Example 1; Bacillus subtilis 6AU-500 (IFO 14407, FERM BP-909) was selected as a line growable on such a medium.

The resistance of this line to pyrimidine analogues is shown in Table 6.

TABLE 6

| Additive to Basic Medium (A) and Quantity (g/ml) | | Growability of Line* 6AU-500 Line |
|---|---|---|
| None | | + |
| 6-azauracil | 200 | + |
| 2-thiouracil | 200 | + |
| 5-fluorouracil | 0.5 | + |
| 5-fluoroorotic acid | 50 | + |

*+: Growth observed

Next, Bacillus subtilis 6AU-500 was cultured under the same conditions as in Example 1. 2.0 mg/ml cytidine was accumulated.

EXAMPLE 5

Using fifty 200 ml flasks each containing 20 ml fermentation medium as shown in Example 1, Bacillus subtilis FU-11 (IFO 14393, FERM BP-908) was cultured as in Example 1. From the culture obtained, microbial cells were removed by centrifugation. The pH value of the supernatant was changed to pH 2.0 with 1N chloric acid solution, and precipitate was removed by centrifugation. Cytidine and deoxycytidine in the supernatant obtained, after adsorption by an activated-charcoal column, were eluted with 50% ethanol solution containing 1.4% ammonia water. Elution fractions of cytidine and deoxycytidine were collected and concentrated under reduced pressure.

The pH value of the liquid concentrate was changed to pH 8.0 with ammonia water; 0.01M potassium borate solution of equal volume was added. Next, cytidine was adsorbed using a Dowex-1×2 column (Cl− type, 200~400 mesh); the column was then washed with distilled water [because deoxycytidine is not adsorbed by this column, it is refined from said column's passing and washing liquids (fraction containing deoxycytidine) in the following procedure].

Cytidine was next eluted from the column using an aqueos solution containing 0.03M potassium chloride and 0.02M potassium borate per liter. Cytidine elution fraction was collected and added to an equal volume of methanol. The fraction was then subjected to repeated concentration to dryness, to remove boric acid. Solid matter obtained was dissolved into a small quantity of water and alcohol added under cool conditions to obtain 3.9 g crude crystal of cytidine. This crystal, after dissolution in a small quantity of hot water, was cooled again to obtain 2.8 g cytidine crystal.

The fraction containing the deoxycytidine was then concentrated to dryness, the solid matter obtained being dissolved in a small quantity of water. Alcohol was added to the solution under cool conditions to obtain 0.8 g crude crystal of deoxycytidine. Next, the crystal, after dissolution in a small quantity of hot water, was cooled again to obtain 0.3 g deoxycytidine crystal.

We claim:

1. A method for the production of cytidine and/or deoxycytidine, which comprises culturing a cytidine deaminase activity-defective microorganism of *Bacillus subtilis* selected from the group consisting of *Bacillus subtilis* AU-50 (FERM BP-907), *Bacillus subtilis* FU-11 (FERM BP-908), *Bacillus subtilis* 6AU-500 (FERM BP-909) and *Bacillus subtilis* 2TU-200 (FERM BP-910), having resistance to at least one member selected from the group consisting of 6-azauracil, 2-thiouracil, 5-fluorouracil, 5-fluoroorotic acid, and their ribosides and ribotides, and with ability to produce cytidine and/or deoxycytidine, in a culture medium to obtain cytidine and/or deoxycytidine produced and accumulated in the culture medium.

2. A method as claimed in claim 1, wherein the microorganism is *Bacillus subtilis* AU-50(FERM BP-907).

3. A method as claimed in claim 1, wherein the microorganism is *Bacillus subtilis* FU-11(FERM BP-908).

4. A method as claimed in claim 1, wherein the microorganism is *Bacillus subtilis* 6AU-500(FERM BP-909).

5. A method as claimed in claim 1, wherein the microorganism is *Bacillus subtilis* 2TU-200(FERM BP-910).

6. A biologically pure culture of a microorganism which is a cytidine deaminase activity-defective *Bacillus subtilis* selected from the group consisting of *Bacillus subtilis* AU-50 (FERM BP-907), *Bacillus subtilis* FU-11 (FERM BP-908), *Bacillus subtilis* 6AU-500 (FERM BP-909) and *Bacillus subtilis* 2TU-200 (FERM BP-910), having resistance to at least one member selected from the group consisting of 6-azauracil, 2-thiouracil, 5-fluorouracil, 5-fluoroorotic acid, and their ribosides and ribotides.

7. A biologically pure culture as claimed in claim 6, wherein the microorganism is *Bacillus subtilis* AU-50 (FERM BP-907).

8. A biologically pure culture as claimed in claim 6, wherein the microorganism is *Bacillus subtilis* FU-11 (FERM BP-908).

9. A biologically pure culture as claimed in claim 6, wherein the microorganism is *Bacillus subtilis* 6AU-500 (FERM BP-909).

10. A biologically pure culture as claimed in claim 6, wherein the microorganism is *Bacillus subtilis* 2TU-200 (FERM BP-910).

* * * * *